United States Patent [19]

Eibl et al.

[11] 4,160,025

[45] Jul. 3, 1979

[54] METHOD OF PRODUCING A BLOOD-COAGULATION-PROMOTING PREPARATION FROM HUMAN BLOOD PLASMA

[75] Inventors: Johann Eibl; Otto Schwarz; Fritz Elsinger, all of Vienna, Austria

[73] Assignee: Immuno Aktiengesellschaft für chemisch-medizinische Produkte, Vienna, Austria

[21] Appl. No.: 822,679

[22] Filed: Aug. 8, 1977

[30] Foreign Application Priority Data

Aug. 30, 1976 [AT] Austria .................................. 6405/76

[51] Int. Cl.² ............................................. A61K 35/16
[52] U.S. Cl. ...................................................... 424/101
[58] Field of Search ........................................ 424/101

[56] References Cited

U.S. PATENT DOCUMENTS

| 3,998,946 | 12/1976 | Condie et al. | 424/101 |
| 4,027,013 | 5/1977 | Bick et al. | 424/101 |

*Primary Examiner*—Sam Rosen
*Attorney, Agent, or Firm*—Brumbaugh, Graves, Donohue & Raymond

[57] ABSTRACT

In a method of producing a blood-coagulation-promoting preparation from human blood plasma, which preparation contains a new blood-coagulating substance called "FEIBA", human plasma with citrate ions is treated with water-insoluble inorganic coagulation-physiologically-surface-active substances in the absence of free calcium ions, thus generating "FEIBA", the water-insoluble substances are separated, the supernatant is treated with basic ion exchangers, wherein "FEIBA" and the coagulation factors II-VII-IX-X adhere to the ion exchangers, and "FEIBA" and the factors II-VII-IX-X are eluted and concentrated.

15 Claims, No Drawings

METHOD OF PRODUCING A BLOOD-COAGULATION-PROMOTING PREPARATION FROM HUMAN BLOOD PLASMA

The invention relates to a method of producing a blood-coagulation-promoting preparation from human blood plasma, which preparation contains a new blood-coagulation-effective substance, called "FEIBA".

This substance influences in a new manner the blood coagulation and causes a bypassing of the factor-VIII-effect, which means that the blood coagulation is normalized without factor-VIII-supply. The preparation is particularly suited for treating haemophilia-A-patients with inhibitor. The abbreviation "FEIBA" stands for "Factor Eight Inhibitor Bypassing Activity".

Haemophilia A is a disease which has been known for a long time, in which the course of blood coagulation is disturbed by the absence of the activity of a blood coagulation factor. This factor is called antihaemophilic factor (AHF) or factor VIII. A cure of this congenital disease that is caused by defective genes as such is not possible. Treatment can only be effected — in case of a haemorrhage — by intravenous supply of corresponding amounts of factor VIII stemming from the blood of healthy donors. While previously one had to use full blood or full plasma, respectively, great amounts of which had to be applied, there are now preparations which contain the factor VIII in concentrated and also in stable, freeze-dried form. In most cases the treatment with these preparations causes the bleeding to stop quickly.

There are, however, also patients in whom not only the factor-VIII-activity is missing, but who also have an inhibitor directed against factor VIII, which inhibitor — depending on the amount present — destroys the effect of the factor VIII supplied, by neutralisation (inhibition). With these factor-VIII-inhibitor-patients so far there has been little hope for a successful treatment. The only possibility consisted in the removal of the inhibitor prior to the treatment with factor-VIII-concentrates, which is only possible by a plasma exchange of the patient's plasma for the plasma of a healthy donor or for plasma substitutes; this requires a complex technical and medical procedure. Before a new treatment, the plasma exchange has to be repeated, since the inhibitor — in particular after the supply of new factor VIII as antigen by a "booster effect" — forms again. A treatment of the inhibitor patients with so-called "immune suppressives" for suppressing the in vivo synthesis of the inhibitor has hitherto been without success in most cases.

Recently there has been a new possibility of treating factor-VIII-inhibitor-patients. Kurczynski and Penner, New Engl. J. Med., vol. 291, pp. 164-167, 1974, were the first to report on a successful treatment of factor-VIII-inhibitor-patients with so-called "activated" prothrombin complex concentrates. Also in publications by Sultan, Brouet and Debre, New Engl. J. Med., vol. 291, p. 1087, 1974, and Abildgaard, Britton and Roberts, Blood, vol. 44, p. 933, 1974, clinically successful applications of activated prothrombin complex preparations in bleeding factor-VIII-inhibitor-patients are reported.

The so-called activation of these prothrombin complex concentrates is probably due to unknown impurities. The preparations could not be tested as regards their effective principle and could not be standardized. Therefore the results are not safe and can hardly be repeated.

The invention aims at overcoming the above described disadvantages and difficulties and has as its object to provide a preparation which safeguards in a repeatable and deliberate manner a generation of the desired factor-VIII-inhibitor-bypassing-activity. The factor-VIII-inhibitor-bypassing-activity is to be measurable by means of a suitable test system and standardizable. The preparation is to be clinically effective and compatible, i.e. it is to stop the bleeding in bleeding factor-VIII-inhibitor-patients and is not to have any undesired side effects.

According to the invention, this object is achieved in that human plasma containing citrate ions is treated in the absence of free calcium ions with water-insoluble inorganic coagulation-physiologically-surface-active substances, such as silica gel or kaolin, wherein the new substance is generated, thereupon the water-insoluble substances are separated and then the supernatant is treated in a manner known per se with basic ion exchangers, such as diethyl amino ethyl groups-containing high molecular substances, wherein the substance "FEIBA" is adsorbed thereon together with the factors II-VII-IX-X, whereupon they are eluted and concentrated. The new substance with the FEIB activity is a protein with a higher molecular weight than that of the unactivated factors II,VII,IX,X (prothrombin complex). While the latter factors have a molecular weight of approximately 70,000, the new substance has a molecular weight in the region of approximately 100,000.

As starting material for the production of the new preparation human citrated plasma is used, which contains all the coagulation factors in native form; furthermore, also plasma fractions can be used which are developed after separation of the factor VIII (AHF), such as e.g. a plasma supernatant of cryoprecipitate or of precipitate I according to Cohn all of which are plasmas that will not coagulate when treated with the water-insoluble inorganic coagulation-physiologically-surface-active substance.

Advantageously, the generation of the substance FEIBA takes place under maintenance of a pH range of between 5.5 and 8.5 and a temperature of between 0° and 30° C.

Suitably, herein the water-insoluble inorganic coagulation-physiologically-surface-active substances are used in an amount of between 0.05 and 5%, preferably between 0.1 and 1%, based on the amount of plasma.

For treating the plasma, substances can be used mainly consisting of fine particles of silicon dioxide, e.g. substances from the group of the diatomaceous earths, such as celite, or substances composed of silicon dioxide and aluminum oxide, e.g. kaolin. In general, substances are suitable which are known as "surface-active" in the coagulation system or which, due to their surface activity, can introduce the contact phase of the blood coagulation. While the coagulation factors which are surface activatable due to these substances (factors XI and XII) are adsorbed in their activated form at this step, the factors II,VII,IX,X together with the generated substance FEIBA remain in the supernatant and can, by using known methods, and after separation of the surface-active, water-insoluble substances be separated and enriched, respectively. For the latter step e.g. weakly basic ion exchangers can be used; diethyl-amino-ethyl (DEAE)-groups-containing, high molecular substances, e.g. DEAE bound to cellulose or cross-linked dextrans, have proved especially successful. The protein fraction which then contains the FEIB-activity in purified and enriched form, can be isolated by adsorption to the above mentioned ion exchangers, washing and elution of the adsorbed plasma proteins having increased ionic strength. After removal of the salts by dialysis and subsequent freeze drying the raw fraction containing the FEIB-activity is obtained in dry, stable form. From this there results the final preparation by dissolving it again in water, adding salts, adjusting the pH, sterile filtrating and freeze-drying it again.

Examinations of the properties of the preparation produced according to the invention showed that the factors IIa (thrombin) and Xa do not contribute anything to the FEIB-activity. Traces of thrombin, as it can be found in the preparation produced according to the invention, do not lead to a shortening of the activated partial thromboplastin time of factor-VIII-inhibitor-plasma. Also soy bean trypsin inhibitor — a well known inhibitor of factor Xa activity — does not inhibit the FEIB-activity of the preparation. On the basis of gel-chromatographic tests it has proved that the new substance has a higher molecular weight than the known factors of the prothrombin complex II,VII,IX and X. Since furthermore the activated factors of the prothrombin complex are formed by enzymatic splitting off of a fraction of the respective native (not-activated) coagulation factor, and thus smaller molecules are formed than the molecules of the corresponding unactivated factors, one can be sure that the FEIB-activity in the preparation produced according to the invention is not caused by an activated factor of the prothrombin complex, but by the newly generated substance having the higher molecular weight.

For characterizing the new substance, on the one hand the ratio of the activities of the coagulation factors II,VII,IX and X to the FEIB-activity can be utilized: This ratio, expressed in units, lies between 0.1 and 10, preferably between 0.5 and 2, wherein one unit of factor II-VII-IX-X corresponds to the activity of these factors which on an average is contained in 1 ml of fresh human citrated plasma, and one FEIBA-unit is defined as that FEIB-activity which reduces the activated partial thromboplastin time of a high titer factor-VIII-inhibitor-plasma to half of the blank value. On the other hand, for characterizing the new substance, also its amidolytic activity can be utilized. Amidolytic activity means the ability of a substance to split off the p-nitroaniline in standardized peptide compounds which are connected via an amide bond with the chromophore p-nitroaniline; the p-nitroaniline is photometrically determined. Such standardized peptide preparations are produced e.g. by KABI company in Sweden; thus the peptide S-2160 N-benzoyl-L-phenylalanyl-L-valyl-L-arginine-p-nitroanilide.HCl (short form: Bz-Phe-Val-Arg-p-nitroanilide.HCl) is specific for thrombin, S-2222 N-benzoyl-L-isoleucyl-L-glutamyl-L-glycyl-L-arginyl-p-nitroanilide.HCl (short form: Bz-Ile-Glu-Gly-Arg-p-nitroanilide.HCl) for Xa and S-2251 D-valyl-L-leucyl-L-lysyl-p-nitroanilide.2HCl (short form: D-Val-Leu-Lys-p-nitroanilide.2HCl) for plasmin. If one examines the preparation produced according to the invention relative to the above-mentioned substrates, a negligibly small amount of amidolytic activity is found. On the other hand, an examination of a preparation having a content of thrombin and/or factor Xa, if they are adjusted to the same FEIB-activity, which the preparation produced according to the invention shows, show a high amidolytic activity.

A further feature of the preparation according to the invention resides in that it has only a very slight thrombin activity, if any at all. The ratio of the thrombin activity to the FEIB-activity does not exceed 0.02, the thrombin activity being expressed in NIH-units (NIH = U.S. National Institute of Health) and the FEIB-activity is expressed in FEIBA-units.

The method according to the invention and the properties of the preparation prepared according to it are explained in more detail by the following examples and test results:

EXAMPLE 1

Fresh frozen plasma is thawed at between 0° and +4° C. and the cryoprecipitate formed therein is separated by centrifugation. The cryo supernatant is adjusted with 0.5 N hydrochloric acid to pH 7.0, 5 g of kaolin per 1 liter cryo supernatant are added and the mixture is stirred at +4° C. for one hour. Thereupon kaolin is separated by centrifuging. The generated substance FEIBA is then adsorbed to DEAE-Sephadex — together with the factors of the prothrombin complex.

For this purpose, 0.5 g DEAE-Sephadex A-50 were added per 1 l of kaolin supernatant and stirred for half an hour at +4° C. The DEAE-Sephadex is separated; the supernatant plasma can be used for preparing gamma globulin and albumin; DEAE-Sephadex is subjected to a double washing process with a trisodium citrate-sodium chloride solution, a pH-value of 7.5 being maintained.

For elution, the DEAE-Sephadex is stirred for 20 minutes with 3% sodium chloride, 0.1% trisodium citrate.2H$_2$O (2% of the original plasma volume), and the eluate is obtained by filtration. The latter is dialysed over night against 0.05% trisodium citrate.2H$_2$O, 0.1% sodium chloride solution at pH 7.0 at +4° C., then frozen and subjected to a first lyophilization process (bulk). In the bulk-material the FEIB-activity as well as the activity of the factors of the prothrombin complex are determined.

For producing the pharmaceutically acceptable preparation with FEIB-activity, the ratio of the units of factor II-VII-IX-X to FEIBA-units is to be between 0.5 and 2; this can be effected by mixing of suitable bulk-batches. The bulk-material is dissolved with distilled, pyrogen-free water, so that the FEIB-activity amounts to between 10 and 50 FEIBA-units per ml (in the present case 25 FEIBA-units per ml). After addition of the salts required for an isotonic solution and adjusting the pH to between 7.0 and 7.5, the solution is cleared through membrane filters and is finally sterile filtered through an 0.2 $\mu$m membrane filter. The solution is filled into the final containers under sterile conditions in 20 ml portions, deepfrozen and lyophilized.

EXAMPLE 2

As starting material, again fresh frozen plasma or cryo supernatant resulting therefrom, respectively, is used. To the cryo supernatant, without a pH-adjustment (native pH = 7.8), 10 g of celite 512 per 1 liter of cryo supernatant are added and stirred for 3 hours at +4° C. After separation of the celite by centrifuging, the preparation containing the generated FEIBA is worked up in the same manner as in Example 1.

On the final preparations, beside the usual safety tests for sterility, general safety, freedom from pyrogens, and absence of HB$_s$-antigen, tests for potency (FEIB-activity), the content of prothrombin complex factors, thrombin content as well as amidolytic activity with the three substrates S-2160, S-2222 and S-2251 were carried out.

The tests were carried out in the manner set forth below:

1. Potency test (determination of the FEIBA-units)

(a) Reagents

Factor-VIII-inhibitor plasma

Citrated plasma of a patient with haemophilia A with an inhibitor against factor VIII (inhibitor titer at least 10 units per ml), lyophilized. During the test period, the inhibitor plasma is put into an ice bath.

Phospholipid-kaolin-suspension

The phospholipid-concentrate (Tachostyptan, Hormon Chemie München) is diluted 1:200 in Owren's buffer, and 0.5% kaolin w/v (0.5 g per 100 ml) are added thereto. The mixture is stored in deep-frozen condition. During the test period it is maintained at room temperature. Citrated saline solution as diluent for samples: 0.7% sodium chloride/0.7% sodium citrate . 2H$_2$O m/20 calcium chloride: During the test period it is maintained at 37° C.

(b) Test method

After dissolution of the FEIBA preparation to be examined and a FEIBA standard preparation with defined FEIBA-units per ml in the given amount of distilled water, 6 geometrical dilutions are prepared by using the citrated saline solution, beginning with 5 FEIBA-units per ml. These dilutions are kept in an ice bath during the test period. The reagents are pipetted in the following manner in glass tubes:

0.05 ml factor-VIII-inhibitor-plasma
0.05 ml sample (dilutions of the test samples and the standard, as well as citrated saline solution as blank value)
0.05 ml phospholipid kaolin suspension
incubation for 6 minutes at 37° C.
0.05 ml m/20 calcium chloride The time from the addition of calcium chloride to the clot formation is timed by a timer (tilting of the test tube or application of an automatic coagulometer).

(c) Calculation of the FEIBA-units per bottle

A calibration curve is made in that the coagulation times (in seconds) of the dilutions of the FEIBA-standard preparation are plotted against the corresponding concentrations (in FEIBA-units per ml) on double logarithmic graph paper. The FEIB-activities of the test sample dilutions are calculated by using the calibration curve and by multiplying with the respective dilution factor. The mean value of these results corresponds to the FEIB-activity of the test sample, expressed in FEIBA-units per ml. If this value is multiplied by the solution volume (in ml), the total amount of the FEIBA-units per bottle is obtained.

2. Determination of the activity of the coagulation factors II, VII, IX and X (A) Factor-II-determination (a) Reagents Serum: Blood of a healthy donor (without anticoagulant) is incubated for 24 hours at 37° C. From the coagulated blood, the serum is removed, centrifuged, portioned and stored in deep-frozen condition. Bovine oxalate plasma absorbed with barium sulfate (as source for factor V and as diluent for samples): Nine parts of bovine blood are mixed with one part of 1.34% sodium oxalate. The resulting plasma is absorbed with 10% barium sulfate. After centrifuging the absorbed plasma is portioned and stored in deep-frozen condition. "Thromborel" (calcium-containing human thromboplastin) Behringwerke AG, Marburg-Lahn.

(b) Test method

The reagents (they are stored in an ice bath during the test, except for Thromborel) are pipetted in glass tubes in the following manner:

0.05 ml serum
0.05 ml sample (serial dilutions of the sample to be tested or of a "normal plasma" or of a standard)
incubation for one minute at 37° C.
0.2 ml Thromborel (is to be maintained at 37° C. during the test)

The time from the addition of Thromborel to the clot formation is timed by a timer.

(c) Calculation of the factor-II-concentration

From pooled plasma samples of at least 15 healthy donors a standard plasma is prepared. This "pool plasma" stands as "normal plasma" and its factor-II-activity is taken to be 100%. Then a calibration curve is made by plotting the coagulation times of the dilution series of this pooled plasma (undiluted, 1:2, 1:4, 1:8, ...) against the corresponding concentrations on double logarithmic graph paper. The factor-II-concentration of the test sample dilutions are expressed in percent of the normal plasma by using the calibration curve and multiplied by the respective dilution factor. The average value of these results corresponds to the activity of the test material in percent of the factor II. The amount of the factor II present in one bottle is calculated according to the following formula:

$$\text{units factor II} = \frac{(\% \text{ factor-II-concentration}) \times (\text{volume in ml})}{100}$$

One unit factor II is equivalent to that factor-II-activity which on an average is present in 1 ml of fresh citrated plasma.

(B) Factor-VII-determination (a) Reagents

Factor-VII-deficient-plasma: citrated plasma of a patient having a severe factor-VII-deficiency (factor VII below 1%), stored in deep-frozen condition or lyophilized after the addition of 1% weight/volume HEPES, with a pH-value of 7.0. Citrated saline solution as diluent for the samples: 0.7% trisodium citrate . 2 H$_2$O, 0.7% sodiumchloride. "Thromborel" (calcium-containing human thromboplastin) of Behringwerke AG, Marburg/Lahn.

(b) Test method

The deficient plasma and the dilutions of the sample are stored in an ice bath. "Thromborel" is kept at 37° C. during the examination.

The reagents are pipetted in glass tubes in the following manner 0.05 ml factor-VII-deficient plasma
0.05 ml sample (serial dilutions of the sample to be tested, or of a "normal plasma" or of a standard, respectively)
incubation for one minute at 37° C.
0.2 ml "Thromborel"

The time from the addition of "Thromborel" until the clot formation is taken with a timer.

(c) Calculation of the factor-VII-concentration

The calculation of the factor-VII-concentration is carried out in the same manner as described for factor II.

(C) Factor-IX-determination (a) Reagents

Factor-IX-deficient-plasma: citrated plasma of a patient with severe haemophilia-B (Factor IX below 1%), stored in deep-frozen condition. Phospholipid/kaolin-suspension: Phospholipid concentrate (Tachostyptan, Hormon Chemie Munchen) is diluted 1:200 in Owren's buffer, kaolin is added (0.5 g per 100 ml) and it is stored in deep-frozen condition. Bovine oxalate plasma, absorbed with barium sulfate, as diluting agent for samples: 9 parts bovine blood are mixed with one part 1.34% sodium oxalate. The resulting plasma is absorbed with 10% barium sulfate. After centrifugation, the absorbed plasma is portioned and stored in deep-frozen condition. m/20 calcium chloride (b) Test method Incubation of factor-IX-deficient-plasma with phospholipid/kaolin suspension: The required amount of deficient plasma is mixed with an equal volume of phospholipid/kaolin suspension, incubated at 37° C. for 5 minutes and then stored in an ice bath for 30 minutes. The reagents (they are kept in an ice bath during the test, except for calcium chloride) are pipetted in glass tubes in the following manner:

0.2 ml incubated deficient plasma-phospholipid/koalin-suspension
0.1 ml sample (serial dilutions of the sample to be tested or of a "normal plasma" or of a standard, respectively)
incubation for one minute at 37° C.
0.1 ml m/20 calcium chloride (is to be maintained at 37° C. during the test)

The time from the addition of calcium chloride up to the clot formation is taken with a timer.

(c) Calculation of factor-IX-concentration

The calculation of the factor-IX-concentration is effected in the same manner as described for factor II.

(D) Factor-X-determination (a) Reagents

Factor-X-deficient plasma: citrated plasma of a patient having a severe factor-X-deficiency (factor X below 1%) is stored in deep-frozen condition or is lyophilized after addition of 1% HEPES and adjustment of the pH-value to 7.0.

Citrated saline solution as diluent for samples: 0.7% sodium chloride/0.7% sodium citrate . 2 $H_2O$ "Thromborel" (calcium-containing human thromboplastin), Behringwerke AG, Marburg/Lahn.

(b) Test method

The reagents (they are kept in an ice bath during the test, except for Thromborel) are pipetted in glass tubes in the following manner:

0.05 ml factor-X-deficient plasma
0.05 ml sample (serial dilutions of the sample to be tested or of the "normal plasma" or of a standard, respectively)
incubation at 37° C. for one minute
0.2 ml Thromborel (is to be maintained at 37° C. during the test).

The time from the addition of Thromborel until the clot formation is taken with a timer.

(c) Calculation of a factor-X-concentration:

The calculation of the factor-X-concentration is effected in the same manner as described for factor II.

3. Thrombin test (a) Reagents

1% fibrinogen solution of human origin Standardized thrombin (Topostasin, Roche, 3000 NIH-thrombin-units per bottle)
0.7% sodium chloride/0.7% sodium citrate . 2 $H_2O$ as diluent (citrated saline solution)

(b) Test method

After dissolution of the lyophilized product in the stated amount of distilled water, six geometrical dilutions are prepared by using citrated saline solution and eight geometrical dilutions of the standardized thrombin, wherein one starts with 1 NIH-unit per ml.

Test method:
0.2 ml 1% fibrinogen solution and
0.2 ml sample (serial dilutions of the sample to be tested and thrombin dilutions as well as a blank value with citrated saline solution) are incubated at 37° C. The time until the clot formation is taken by tilting the test tubes at increasing intervals, i.e. from 10 minutes up to one hour. This procedures lasts for at least 6 hours. A final tilting of the tubes is carried out after incubation over night. The blank value (diluent as sample) is to remain stable over night (no clot formation).

(c) Calculation of the thrombin-concentration

A calibration curve is made in that the coagulation times of the geometrical dilutions of the standard thrombin are plotted against the corresponding concentration (thrombin units per ml) on double logarithmic graph paper. The thrombin concentration of the test sample dilutions are calculated by using the calibration curve and by multiplication with the respective dilution factor. The mean value of these results corresponds to the thrombin activity of the test sample, expressed in thrombin units per ml. If this value is multiplied by the solution volume in ml, the total amount of the thrombin units per bottle is obtained.

4. Determination of the amidolytic activity (a) Reagents

Chromogenic substrates:

S-1260: N-benzoyl-L-phenylalanyl-L-valyl-L-arginine-p-nitroanilide.HCl
(short form: Bz-Phe-Val-Arg-p-nitroanilide.HCl)
0.5 mg/ml $H_2O$ = 0.73 m molar S-2222: N-benzoyl-L-isoleucyl-L-glutamyl-L-glycyl-L-arginyl-p-nitroanilide.HCl
(short form: Bz-Ile-Glu-Gly-Arg-p-nitroanilide.HCl)
1.4 mg/ml $H_2O$ = 1.91 m molar S-2251: D-valyl-L-leucyl-L-lysyl-p-nitroanilide . 2HCl
(short form: D-Val-Leu-Lys-p-nitroanilide . 2HCl)
1.65 mg/ml $H_2O$ = 2.99 m molar Buffer:
6.06 g "Tris" (tris(hydroxymethyl)-aminomethane) = 0.05 molar
10.6 g sodium chloride = 0.18 molar
Dissolve with 1 liter distilled water. The pH-value is adjusted with concentrated hydrochloric acid to 7.4.

(b) Test method 1.0 ml buffer
0.1 ml test sample (preparation containing FEIBA)
0.2 ml substrate (S-2160 or S-2222 or S-2251, respectively).

This mixture is filled into a 1 cm cuvette which can be thermostated at 37° C., and in a photometer at 405 nm the increase of the optical density is measured at time intervals of 1 minute.

(c) Evaluation:

From at least 5 individual measurements the average increase of the optical density per minute is calculated and multiplied by 1000; this value is denoted by $\Delta$ OD.$10^3$/min and serves for characterising the amidolytic activity (enzyme activity) of the sample examined as regards the respective substrate used. If the $\Delta$ OD.$10^3$/min-values are divided by the activity of the test sample in FEIBA-units per 0.1 ml (sample amount used) and in factor II,VII,IX,X-units per 0.1 ml, respectively, there results a "specific amidolytic activity" characteristic of the respective test sample - under the test conditions mentioned — i.e. the $\Delta$ OD.$10^3$/min-value related to 1 unit FEIBA or 1 unit factor II,-VII,IX,X, respectively.

The preparations produced according to Examples 1 and 2 showed the properties listed in the table during the tests carried out as described above.

Table:

| Filling or dissolution volume, respectively | Example 1 20 ml | Example 2 20 ml |
|---|---|---|
| FEIBA-units per bottle | 470 | 280 |
| Factor-II-units per bottle | 610 (1.30) | 240 (0.86) |
| Factor-VII-units per bottle | 520 (1.11) | 260 (0.93) |
| Factor-IX-units per bottle | 700 (1.49) | 300 (1.07) |
| Factor-X-units per bottle | 540 (1.15) | 210 (0.75) |
| Thrombin NIH-units per bottle | 1.4 (0.003) | 1.0 (0.004) |
| Amidolytic activites ($\Delta$OD.$10^3$/min) | | |
| S-2160 | 1 (0.43) | 1 (0.71) |
| S-2222 | 3 (1.28) | 2.5 (1.79) |
| S-2251 | 4 (1.70) | 2 (1.43) |

The figures in parentheses give the respective ratio to the FEIBA-units. With the amidolytic activities, the figure in parentheses is the "specific amidolytic activity", i.e. the respective $\Delta$OD.$10^3$/min-value per one FEIBA-unit inserted in the above described test system.

What we claim is:

1. A method of producing a blood-coagulation promoting preparation having Factor VIII inhibitor bypassing activity comprising treating plasma containing coagulation Factors II, VII, IX and X in in the absence of free calcium ions with a water-insoluble inorganic coagulation-physiologically-surface-active substance selected from the group consisting of diatomaceous earths and substances composed of silicon dioxide and aluminum oxide to generate the Factor VIII inhibitor bypassing active (FEIBA) substance, said plasma being non-coagulating when treated with said surface-active substance; separating the water-insoluble substances; treating the supernatant with a basic ion exchanger to adsorb the FEIBA substance and said coagulation Factors II, VII, IX and X; eluting the FEIBA substance and the coagulation factors II, VII, IX and X from the basic ion exchanger; and concentrating the FEIBA substance and coagulation Factors II, VII, IX and X.

2. A method as set forth in claim 1, wherein said new substance FEIBA is generated while maintaining a pH-value of from 5.5 to 8.5, and a temperature of from 0° to 30° C.

3. A method as set forth in claim 1, wherein said water-insoluble, inorganic coagulation-physiologically-surface-active substances are used in an amount of from 0.05 to 5%, based on the amount of plasma used.

4. A method as set forth in claim 1, wherein said water-insoluble, inorganic coagulation-physiologically-surface-active substances are used in an amount of from 0.1 to 1%, based on the amount of plasma used.

5. The method according to claim 1, wherein the plasma is selected from the group consisting of citrated plasma, cryosupernatant of frozen plasma, and plasma supernatant of Cohn's precipitate I.

6. A method according to claim 1, in which the basic ion exchanger is a high molecular weight substance containing diethylaminoethyl groups.

7. A method as set forth in claim 1, wherein said water-insoluble inorganic coagulation-physiologically-surface-active substance is celite.

8. A method as set forth in claim 1, wherein said water-insoluble inorganic coagulation-physiologically-surface-active substance is kaolin.

9. A preparation having Factor VIII inhibitor bypassing activity containing as an active ingredient in an amount effective to provide said Factor VIII inhibitor bypassing activity, a Factor VIII inhibitor bypassing active (FEIBA) substance which is produced by treating plasma containing coagulation Factors II, VII, IX and X in the absence of free calcium ions with a water-insoluble inorganic-coagulation-physiologically-surface-active substance selected from the group consisting of diatomaceous earths and substances composed of silicon dioxide and aluminum oxide to generate the FEIBA substance, said plasma being non-coagulating when treated with said surface-active substance; separating the water-insoluble substances; treating the supernatant with a basic ion exchanger to adsorb the FEIBA substance and said coagulation Factors II, VII, IX and X; eluting the FEIBA substance and the coagulation Factors II, VII, IX and X from the basic ion exchanger; and concentrating the FEIBA substance and coagulation Factors II, VII, IX and X.

10. A preparation according to claim 9 wherein there is a certain ratio between the activities of the coagulation factors II-VII-IX-X and the FEIB-activity, said ratio being expressed in units, one unit of the coagulation factors II-VII-IX-X corresponding to the activity of the coagulation factors II-VII-IX-X contained on an average in 1 ml of fresh human citrated plasma, and one FEIBA-unit corresponding to that FEIB-activity which reduces the activated partial thromboplastin time of a high-titer factor-VIII-inhibitor-plasma to half of the blank value, and wherein said ratio is between 0.1 and 10.

11. A preparation as set forth in claim 10, wherein said ratio is between 0.5 and 2.

12. A preparation according to claim 9 wherein the specific amidolytic activity as regards the substrates N-benzoyl-L-phenylalanyl-L-valyl-L-arginine-p-nitroanilide.HCl, N-benzoyl-L-isoleucyl-L-glutamyl-L-glycyl-L-arginyl-p-nitroanilide.HCl, D-valyl-L-leucyl-L-lysyl-p-nitroanilide.2HCl, i.e. $\Delta$ OD.$10^3$/min-values per 1 FEIBA-unit do not exceed 4, and $\Delta$OD.$10^3$/min-values per 1 unit of coagulation factor II-VII-IX-X activity do not exceed 3, one unit of the coagulation factors II-VII-IX-X corresponding to the activity of the coagulation factors II-VII-IX-X contained on an average in 1 ml of fresh human citrated plasma, and one FEIBA-unit corresponding to that FEIB-activity which reduces the activated partial thromboplastin time of a high-titer factor-VIII-inhibitor-plasma to half of the blank value.

13. A preparation according to claim 9, wherein the specific amidolytic activity as regards the substrates N-benzoyl-L-phenylalanyl-L-valyl-L-arginine-p-nitroanilide.HCl, N-benzoyl-L-isoleucyl-L-glutamyl-L-glycyl-L-arginyl-p-nitroanilide.HCl, D-valyl-L-leucyl-L-lysyl-p-nitroanilide.2HCl, i.e. $\Delta$ OD.$10^3$/min-values per 1 FEIBA-unit are less than 3, and $\Delta$ OD.$10^3$/min-values per 1 unit of coagulation factor II-VII-IX-X activity are less than 2, one unit of the coagulation factors II-VII-IX-X corresponding to the activity of the coagulation fractors II-VII-IX-X contained on an average in 1 ml of fresh human citrated plasma, and one FEIBA-unit corresponding to that FEIB-activity which reduces the activated partial thromboplastin time of a high-titer factor-VIII-inhibitor-plasma to half of the blank value.

14. A preparation according to claim 9 wherein the ratio of thrombin activity to FEIB-activity does not exceed 0.02, the thrombin activity being expressed in NIH-units and the FEIB-activity being expressed in FEIBA-units, one FEIBA-unit corresponding to that FEIB-activity which reduces the activated partial thromboplastin time of a high-titer factor-VIII-inhibitor-plasma to half of the blank value.

15. A method for promoting the coagulation of blood containing an inhibitor to Factor VIII which comprises administering to a patient having blood containing an inhibitor to Factor VIII, an amount, effective to provide Factor VIII inhibitor by-passing activity, of a Factor VIII inhibitor by-passing active (FEIBA) preparation which is produced by treating plasma containing coagulation Factors II, VII, IX and X with a water-insoluble inorganic coagulation-physiologically-surface-active substance selected from the group consisting of diatomaceous earths and substances composed of silicon dioxide and aluminum oxide to generate the FEIBA substance, said plasma being non-coagulating when treated with said surface active substance; separating the water-insoluble substances; treating the supernatant with a basic ion exchanger to adsorb the FEIBA substance and the coagulation Factors II, VII, IX and X; eluting the FEIBA substance and said coagulation Factors II, VII, IX and X from the basic ion exchanger; and concentrating the FEIBA substance and said coagulation Factors II, VII, IX and X.

* * * * *

UNITED STATES PATENT AND TRADEMARK OFFICE
CERTIFICATE OF CORRECTION

PATENT NO. : 4,160,025
DATED : July 3, 1979
INVENTOR(S) : Eibl et al.

It is certified that error appears in the above-identified patent and that said Letters Patent are hereby corrected as shown below:

Col. 5, line 9, after "plasma" insert a colon (-- : --); line 14, after "suspension" insert a colon (-- : --); line 20, "Citrated ..." should start a new line; line 21, "0.7% sodium" (first occurrence) should start a new line; line 22, "m/20 ..." should start a new line; line 22, "During the ..." should start a new line; line 64, "Bovine" should start a new line. Col. 6, line 48, "Citrated ..." should start a new line; line 50, "'Thromborel'" should start a new line. Col. 7, line 8, "Phospholipid ..." should start a new line; line 18, "m/20 ..." should start a new line. Col. 8, line 4, "Standardized" should start a new line. Col. 11, line 12, "fractors" should read --factors--.

Signed and Sealed this

Sixteenth Day of October 1979

[SEAL]

Attest:

RUTH C. MASON
Attesting Officer

LUTRELLE F. PARKER
Acting Commissioner of Patents and Trademarks